(12) United States Patent
Anapliotis

(10) Patent No.: US 9,980,762 B2
(45) Date of Patent: May 29, 2018

(54) BONE SCREW ARRANGEMENT WITH VARIABLE LENGTH

(71) Applicant: Merete Medical GmbH, Berlin (DE)

(72) Inventor: Emmanuel Anapliotis, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 698 days.

(21) Appl. No.: 14/402,603

(22) PCT Filed: Jun. 11, 2013

(86) PCT No.: PCT/DE2013/100209
§ 371 (c)(1),
(2) Date: Nov. 20, 2014

(87) PCT Pub. No.: WO2013/185755
PCT Pub. Date: Dec. 19, 2013

(65) Prior Publication Data
US 2015/0150615 A1    Jun. 4, 2015

(30) Foreign Application Priority Data
Jun. 11, 2012  (DE) .................... 20 2012 005 594 U

(51) Int. Cl.
*A61B 17/86*   (2006.01)
(52) U.S. Cl.
CPC ........ *A61B 17/8685* (2013.01); *A61B 17/863* (2013.01); *A61B 17/8605* (2013.01)
(58) Field of Classification Search
CPC .. A61B 17/8685; A61B 17/844; A61B 17/742
See application file for complete search history.

(56) References Cited

U.S. PATENT DOCUMENTS

| 2,801,631 A | 8/1957 | Charnley |
| 4,940,467 A * | 7/1990 | Tronzo ................. A61B 17/742 606/304 |

(Continued)

FOREIGN PATENT DOCUMENTS

| DE | 69211561 T2 | 10/1996 |
| DE | 102005007674 | 8/2006 |
| WO | 8906940 A1 | 8/1989 |

OTHER PUBLICATIONS

International Preliminary Report on Patentability for PCT/DE2013/100209 dated Dec. 16, 2014.

(Continued)

*Primary Examiner* — Andrew Yang
(74) *Attorney, Agent, or Firm* — Andrus Intellectual Property Law, LLP

(57) ABSTRACT

A bone screw arrangement with a variable length, comprises a guide screw, which is formed with a guide that extends in the axial direction in the interior of the guide screw, and comprises an anchor screw, which has a guide element that is received in the guide such that an arrangement length formed by the guide screw together with the anchor screw can be adjusted by moving the guide element in the axial direction in the guide in the interior of the guide screw. The guide element is received in a free-running manner in a portion of the guide when the guide element is moved in order to change the arrangement length, and the guide element is blocked from running freely in the axial direction at least in a distal end position in which the anchor screw is completely extended.

9 Claims, 4 Drawing Sheets

(56) References Cited

U.S. PATENT DOCUMENTS

Figure 1:
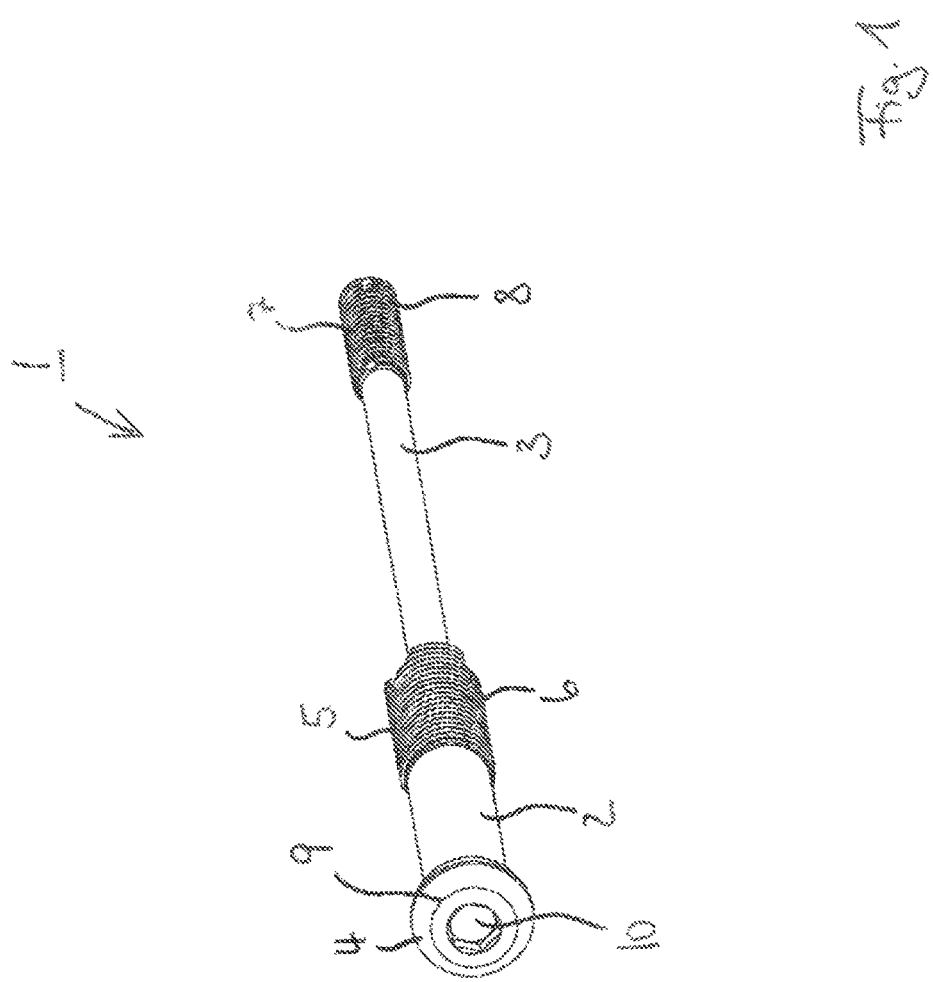

| | | | |
|---|---|---|---|
| 5,964,761 A * | 10/1999 | Kambin | A61B 17/1757 |
| | | | 606/280 |
| 8,403,973 B2 * | 3/2013 | Biyani | A61B 17/8685 |
| | | | 606/309 |
| 2004/0127900 A1 | 7/2004 | Konieczynski et al. | |
| 2005/0143735 A1 | 6/2005 | Kyle | |
| 2005/0245933 A1 | 11/2005 | Sevrain | |
| 2010/0016903 A1 * | 1/2010 | Matityahu | A61B 17/866 |
| | | | 606/301 |
| 2010/0268285 A1 | 10/2010 | Tipirneni | |

OTHER PUBLICATIONS

International Search Report for PCT/DE2013/100209 dated Sep. 16, 2013.

* cited by examiner

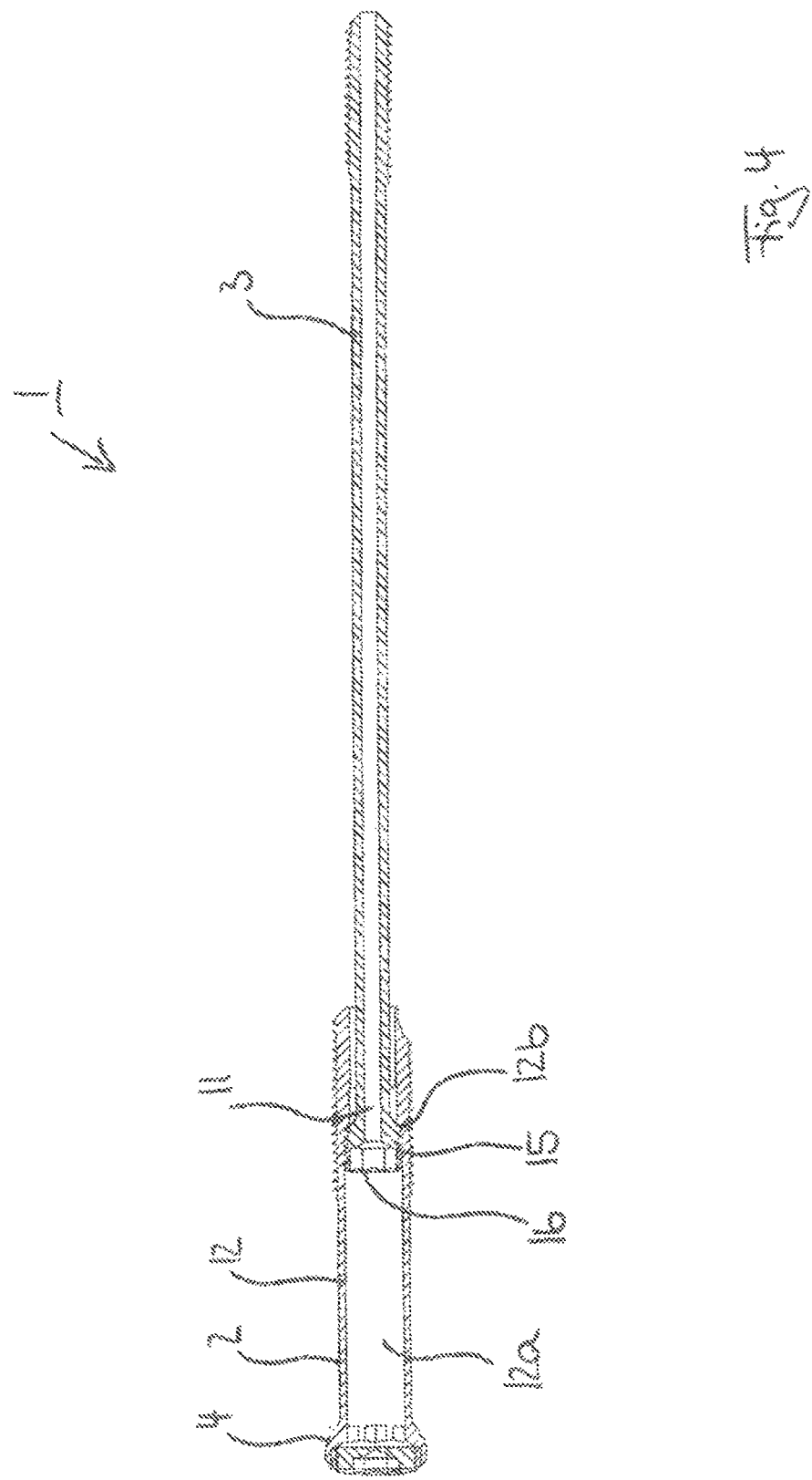

US 9,980,762 B2

BONE SCREW ARRANGEMENT WITH VARIABLE LENGTH

CROSS-REFERENCE TO RELATED APPLICATIONS

This application is the U.S. national stage application of International Application PCT/DE2013/100209, filed Jun. 11, 2013, which international application was published on Dec. 19, 2013, as International Publication WO2013/185755 in the English language. The international application is incorporated herein by reference, in entirety. The international application claims priority to German Patent Application No. 20 2012 005 594.1, filed Jun. 11, 2012, which is incorporated herein by reference, in entirety.

The invention relates to a bone screw arrangement with variable length.

BACKGROUND

Such bone screw arrangements are used for the fixation of bones or bone fragments, particularly in the case of bone fractures, in such a way that the bone screw arrangement adjusts in a dynamic manner to changing conditions during the healing process by changing its length. An example of use would be the treatment of slipped capital femoral epiphysis (SCFE).

A bone screw arrangement with variable length is disclosed in Document WO 8906940 A1. In the prior art arrangement, provision is made of an anchoring screw configured as a bone screw, which is axially displaceably received in a guide formed in the interior of a guide screw. In this manner it is possible for the bone screw arrangement, to change its overall screw length in response to bone growth, for example, when the bone screw arrangement is positioned in a human or animal body. As the overall length changes, a guide element formed at the head end on the anchor screw is guided in the axial direction in the guide. The guide element formed on the anchor screw is configured with a, hex head, which is interlockingly received in the guide on the guide screw such that the anchor screw turns conjointly with the guide screw as the latter is turned.

Document DE 10 2005 007 674 A1 relates to an orthopedic fixation system. In using the system, a bearing sleeve is screwed into a bone plate. In its interior the bearing sleeve receives a bearing screw, which has a bone thread on its distal end. A head of the bearing screw is freely movable in the axial direction in the interior of the bearing sleeve until the head reaches an annular step, which forms a distal stop for the head. The annular step prevents the bearing screw from extending any further.

Document DE 692 11 561 T2 concerns a device for inserting an, implant. The implant comprises a sleeve, into which a bolt portion is screwed. In each relative position, the sleeve and the bolt portion are secured against relative axial displacement by an outer thread on the bolt portion and an inner thread on the sleeve engaging with one another.

Document US 20040127900 A1 concerns a bone plate arrangement in which a bone plate has a plurality of throughholes in which a corresponding bone screw is screwed during the implanting process.

A bone screw arrangement is described in Document US 20050143735 A1, in which a screw shank is inserted in a compression portion in such a way that the outer thread on the screw shank ultimately cooperates with the inner thread on the compression portion.

Document U.S. Pat. No. 2,801,631 also discloses a bone screw arrangement in which a bolt portion has a bone thread on its end. In use, the bolt portion is screwed into a sleeve.

SUMMARY

The object of the invention is to provide an improved bone screw arrangement with variable length that enables both implanting and explanting in an easy and safe manner.

This object is achieved with a bone screw arrangement with variable length as in independent claim 1. Advantageous embodiments of the bone screw arrangement are the subject matter of dependent subordinate claims.

A bone screw arrangement with variable length and with a guide screw and an anchor screw is produced. The guide screw is equipped with a guide, which extends in the interior of the guide screw in the axial direction. A guide element is formed on the anchor screw, which element is received in the guide in such a way that an overall arrangement length formed by the guide screw together with the anchor screw can be adjusted by moving the guide element (which can also be designated as "guide portion") in the axial direction in the guide in the interior of the guide screw. As a result the overlap between the guide screw and the anchor screw changes, becoming greater the further the anchor screw is received in the guide of the guide screw. The greater the overlap of the two screws, the shorter the overall length of the bone screw arrangement.

For the movement of the guide element in the guide in the axial direction that adjusts the overall screw length, said element is received in a free-running manner in a portion of the guide, which in one embodiment can mean that the anchor screw can be inserted in and pulled out of the guide screw without the two screws being turned relative to each other. Received in a free-running manner means in particular that the guide element can be displaced axially in at least one direction, without the guide blocking this axial displacement. In contrast the guide element is blocked from running freely in the axial direction, at least in a distal end position in which the anchor screw is completely extended. In particular a free-running axial shifting, of the guide element out of the distal end position is prevented. This does not necessarily mean that it is impossible to move the anchor screw in the axial direction out of the end position in order to shorten the overall arrangement length, but that such a movement is preferably only possible via forced guidance, wherein a turning of the guide screw or of the anchor screw leads to the forced axial movement of the guide element in the guide, for example.

Preference is given to the guide screw as well as the anchor screw each being configured as a bone screw by providing an outer bone screw thread.

In an embodiment, in terms of its external design the guide element is interlockingly received in the guide.

In the guide, the guide element of the anchor screw is movable to and from a completely retracted and a completely extended position (distal end position), which correspond to the shortest and longest overall arrangement lengths of the bone screw arrangement, respectively. In one embodiment, for example, free-running means that for both screws, their relative axial position to one another (overlap in the axial direction) can be adjusted without another aspect of the relative position being adjusted, in particular the angular positions relative to one another (relative radial position). As an alternative or additionally, there can be a free-running adjustment in the axial direction, provided that it is not necessary to release a locking device on at least one of the two screws in order to achieve this.

For example, provision can be made of an overall guide path in the axial direction of about 20 mm. The overall arrangement length can be varied for different bone screw arrangements by employing anchor screws of different lengths, for example. Furthermore, the axial displacement path in the guide can be of different lengths for different bone screw arrangements.

A development provides for the guide having an additional portion in which the guide element is blocked from axial free-running. In this embodiment, a free-running axial shifting along the additional portion is blocked for the guide element. The additional portion of the guide can extend continuously all the way to the distal end position.

In a configuration, provision can be made such that an inner thread is formed in the additional portion in the guide, which inner thread engages with an outer thread formed on the guide element in order to block the guide element from running freely in the axial direction. Provision can be made such that the inner thread and the outer thread are produced with essentially the same axial lengths. With the turning the guide screw and/or of the anchor screw, the engagement of the inner and outer threads lead to the forcible adjustment of the overall arrangement length, which corresponds to forced guidance of the guide element of the anchor screw in the guide of the guide screw. As a result of the engagement of the inner and outer threads, the relative position between the anchor screw and the guide screw cannot be changed without rotary thread actuation such that the guide element in this zone of the guide, namely the additional guide portion is not arranged in the guide in a free-running manner. Rather, a rotary movement of at least the guide screw or of at least the anchor screw is required for axially displacing the guide element in the guide and thus for altering the overall length of the bone screw arrangement. If the inner thread is in the distal end region of the guide in relation to the screw head of the guide screw, then by means of force-guided displacement of the guide element attains the completely extended position in which the bone screw arrangement has its maximum length. Further turning will then bring about a compulsory conjoint rotation of the guide screw and the anchor screw (i.e., of the entire arrangement) rather than any further length adjustment of the bone screw arrangement. This facilitates removal of the bone screw arrangement from the bone or from a bone compound, for example.

An embodiment provides for the arrangement of the guide element on the screw head of the anchor screw. Provision can be made such that the guide element is formed entirely by the screw head of the anchor screw. Provision can be made such that the outer thread on the guide element only extends over a portion of the screw head.

A development preferably provides for the guide screw having an opening on its head that communicates with the guide. The opening is configured as, for example, a borehole through which the guide in the interior of the guide screw can be accessed via the end face. The borehole can have essentially the same diameter as the guide in the interior of the guide screw, or it can have a smaller diameter.

In a configuration, provision can be made such that the opening on the head end is closed with a detachably mounted cover. Provision can be made such that the cover is received on the guide screw as a countersunk cover.

A development can provide for the detachable mounting of the cover by means of a cover screw thread. Provision can be made such that the cover is screwed into an opening on the end face of the guide screw. Preference is given to the cover being equipped with an exterior insertion opening, into which a screw turning device can be inserted for turning the cover. The insertion opening is produced with, for example, a hexagonal cross-section. In a preferred embodiment, the insertion opening is configured as a hex socket, for example a 5.0 hex socket. By inserting a screw turning device such as an Allen wrench into the insertion opening, the cover can be screwed in and unscrewed, particularly for unblocking the access to the guide in the guide screw.

A development provides for the cover screw thread to run opposite in direction to the screw thread, which is formed with the inner thread in the portion of the guide and with the outer thread on the guide element. Preference is given to configuring the cover screw thread as a left-hand thread.

In a configuration provision can be made such that the screw head of the anchor screw has an insertion opening for a screw turning device, wherein the insertion opening is accessible via the opening on the head of the guide screw. This insertion opening can also be equipped with a hex socket.

An embodiment provides for equipping the guide screw with a bone screw thread in an end region distal to the screw head.

A development preferably provides for equipping the anchor screw with a bone screw thread in an end region distal to the screw head.

DESCRIPTION OF PREFERRED EXEMPLARY EMBODIMENTS

The invention will be described in more detail in the following, with the aid of preferred exemplary embodiments and with reference to figures in a drawing. Shown are:

FIG. 1 a perspective view of a bone screw arrangement.

Figure 2:
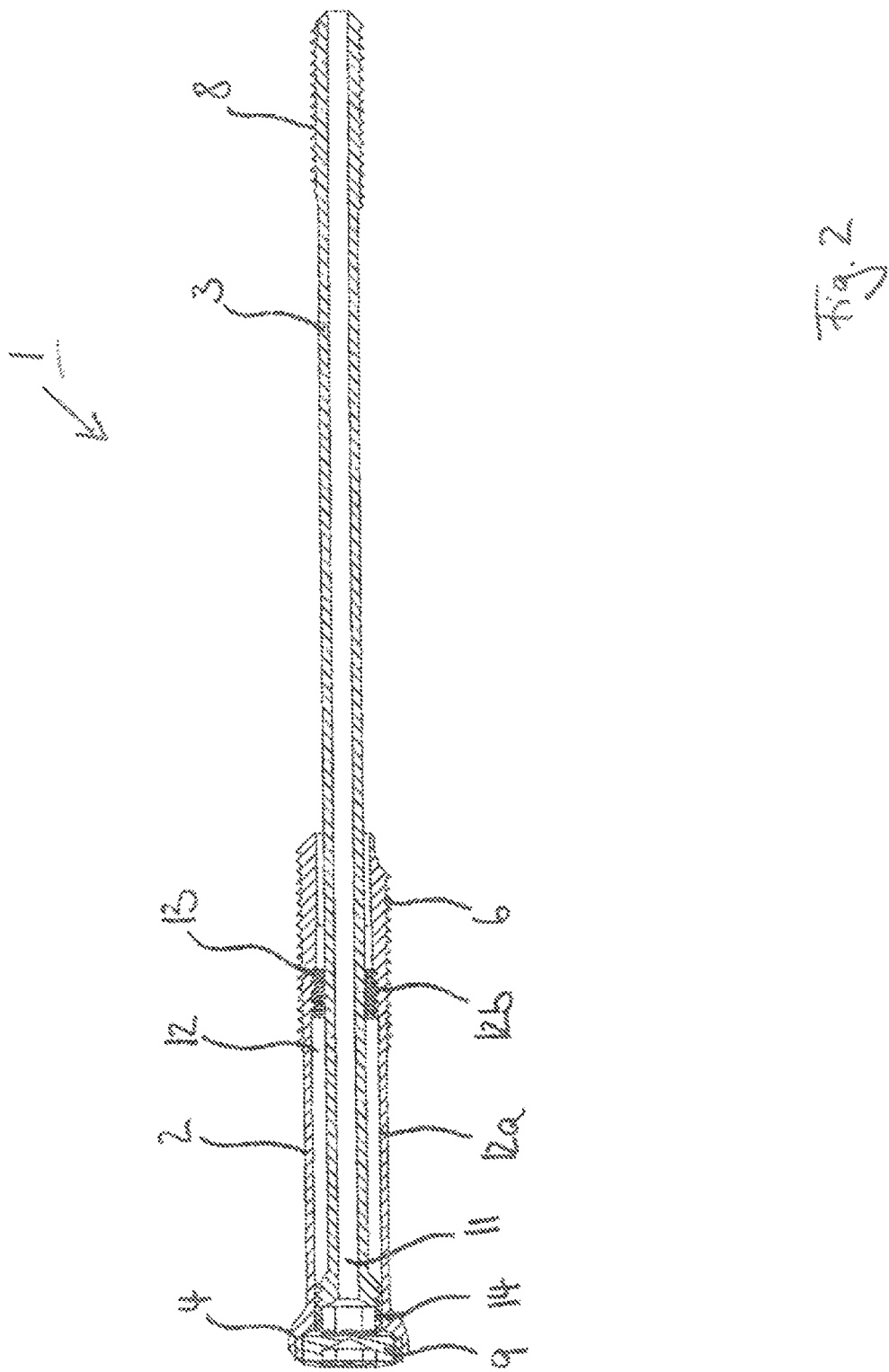

FIG. 2 a schematic illustration in longitudinal section of the bone screw arrangement from FIG. 1 in a starting position.

Figure 3:
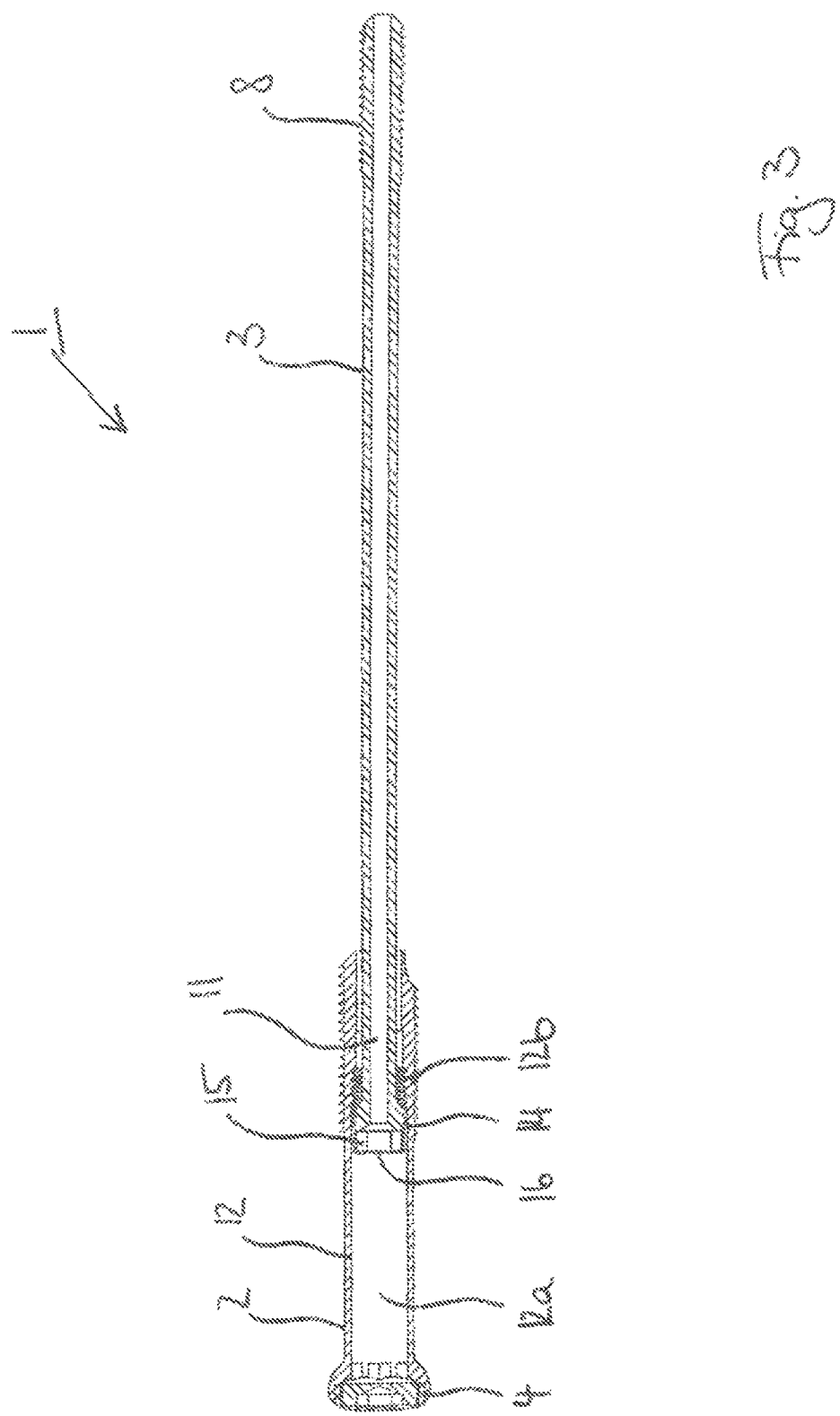

FIG. 3 a schematic illustration in longitudinal section of the bone screw arrangement from FIG. 1 in a position at the end of bone growth, and FIG. 4 a schematic illustration in longitudinal section of the bone screw arrangement from FIG. 1 in a removal position.

FIG. 1 is a schematic illustration of the bone screw arrangement 1 with a guide screw 2 and an anchor screw 3. The guide screw 2 is equipped with a bone screw thread 6 in an end region 5 distal to the screw head 4 of the guide screw 2. The anchor screw 3 is likewise equipped with a bone screw threat 8 in a distal end region 7.

A cover 9 is screwed into the end face of the screw head 4 of the guide screw 2. The cover 9 is equipped with an insertion opening 10, which is formed with a hex socket. A screw turning device such as an Allen wrench can be inserted in the insertion opening 10 for actuating the cover 9.

FIG. 2 is a schematic illustration in longitudinal section of the bone screw arrangement 1. A guide element 11 formed on the anchor screw 3, which can also be designated as a guide portion, is received in an axially displaceable manner in a guide 12 formed in the interior of the guide screw 2. In the example illustrated, the guide 12 is configured as a hollow space extending in the axial direction, in which the anchor screw 3 is guided with the guide element 11, which is preferably interlockingly received herein. In a portion 12a of the guide 12, the guide element 11 is axially displaceable in a free-running manner such that the guide element 11 can slide freely in the portion 12a. The anchor screw 3 and hence the guide element 11 formed thereon are also capable of freely turning in place in the zone of the portion 12a. In the portion 12a the guide 12 forms a tubular receptacle with a smooth surface on which the guide element 11 is freely movable.

In terms of its position relative to the guide screw 2, the anchor screw 3 is displaceable to and from the fully retracted position shown in FIG. 2 and the fully extended position shown in FIG. 4 such that an overall length of the bone screw arrangement can be adjusted in this manner. The arrangement is at its minimum overall length in the position in FIG. 2 and at its maximum overall length in the embodiment according to FIG. 4.

In the portion 12a, the guide element 11 is axially displaceable in a free-running manner in the guide 12. In the embodiment illustrated, the guide element 11 slides freely on the walls of the guide 12 until attaining the position shown in FIG. 3. The latter shows the bone screw arrangement 1 at the end of a process in which the overall length of the bone screw arrangement 1 increases as a result of bone growth in the course of a healing process supported by the bone screw arrangement 1, for example. The bone is thus able to grow freely to the extent permitted by the free-running axial displacement of the guide element 11 in the guide 12.

This free-running is stopped upon attaining the position shown in FIG. 3, in which the guide element 11 is then at the distal end of the portion 12a. A further lengthening of the overall length of the bone screw arrangement 1 is then only possible via forced guidance of the guide element 11. To this end an inner thread 13 formed in a portion 12b on the inner surface of the guide 12 and an outer thread 14 on the guide element 11 engage with one another. By turning the guide screw 2, the guide element 1 is thus moved from the position shown in FIG. 3 into the position shown in FIG. 4, which corresponds to a distal end position in which the bone screw arrangement 1 has its maximum overall length.

If the anchor screw 3 is anchored in a bone, the turning of the guide screw 2 and the cooperation of the inner thread 13 and the outer thread 14 induced thereby preferably leads to a partial unscrewing of the guide screw 2 from the bone, as the guide screw 2 is forcibly moved in a direction away from the distal end of the anchor screw 3. After the relative position between the guide screw 2 and the anchor screw 3 shown in FIG. 4 is attained, a further turning of the guide screw 2 then leads to the unscrewing of the entire bone screw arrangement 1 from the bone. To this end, the guide screw 2 and the anchor screw 3 are fixed in relation to one another as a result of the engagement of the inner thread 13 with the outer thread 14. The inner and outer threads 13, 14 act as counter-threads, thus helping stabilize the unscrewing of the bone screw arrangement 1 for explanation. To this end, a screw turning device engages in the insertion opening 10 on the cover 9.

Provision is made such that a cover screw thread, which is used for mounting the cover 9 on the guide screw 2, runs in a direction opposite to the thread formed with the inner and outer threads 13, 14 so that by turning on the cover 9, the guide screw 2 and the anchor screw 3 assume the relative position to one another shown in FIG. 4 and the entire structure can then be unscrewed from the bone.

FIGS. 2 through 4 show that in the illustrated embodiment, the guide element 11 is formed on the screw head 15 of the anchor screw 3. The screw head 15 is equipped with its own insertion opening 16, which in the embodiment illustrated is likewise equipped with a hex socket, preferably in the size M5. With the cover 9 unscrewed, the insertion opening 16 can be accessed in the guide 12, particularly in order to tighten the anchor screw 3 for implanting the bone screw arrangement 1.

The features disclosed in the present description, in the claims, and in the drawing can be used either individually or in any combination for the realization of different embodiments.

The invention claimed is:

1. A bone screw arrangement with variable length, comprising:
   a guide screw which is formed with a guide that extends in the interior of the guide screw in the axial direction, and
   an anchor screw, which has a guide element that is received in the guide in such a way that an arrangement length formed by the guide screw together with the anchor screw can be adjusted by the guide element being moved the axial direction in the guide in the interior of the guide screw,
   wherein in the movement that adjusts the arrangement length, the guide element is received in a free-running manner in a portion of the guide and blocked from running freely in the axial direction in at least a distal end position in which the anchor screw is completely extended;
   wherein an inner thread is formed in an additional portion in the guide, which engages with an outer thread formed on the guide element in order to block the axial free-running of the guide element,
   wherein the guide screw has an opening on a screw head that communicates with the guide,
   wherein the opening on the screw head is closed with a detachably mounted cover,
   wherein the cover is detachably mounted by means of a cover screw thread, and
   wherein the cover screw thread runs in a direction opposite to a screw thread formed with the inner thread in the portion of the guide and with the outer thread on the guide element.

2. The bone screw arrangement according to claim 1, wherein a screw head of the anchor screw has an insertion opening for a screw turning device, wherein the insertion opening is accessible via the opening on the screw head of the guide screw.

3. The bone screw arrangement according to claim 1, wherein the guide screw is equipped with a bone screw thread in an end region distal to the screw head of the guide screw.

4. The bone screw arrangement according to claim 2, wherein the anchor screw is equipped with a bone screw thread in an end region distal to the screw head of the anchor screw.

5. A screw arrangement for bone comprising:
   an anchor screw having a first end that includes a guide element and an opposing, distal end that includes bone screw threads configured to anchor the anchor screw to bone; and
   a guide screw having bone screw threads configured to engage bone and a guide in which the anchor screw is received such that an overall length of the screw arrangement can be varied, the guide having a first portion in which the guide element freely slides and an additional portion in which the guide element is prevented from freely sliding,
   wherein the overall length of the screw arrangement is fixed when the guide element is in the additional portion, wherein the guide element includes guide element threads, and wherein the additional portion includes inner guide screw threads configured to engage with the guide element threads to thereby fix the overall length of the screw arrangement, wherein the guide screw is rotatable such that the guide element is moved into a maximum overall length position in which the screw arrangement has a maximum overall length, and wherein the guide element threads and the inner guide screw threads act as counter-threads such that further rotation of the guide screw after the guide element is moved into the maximum overall length position causes the screw arrangement to unscrew from the bone.

6. The screw arrangement according to claim 5, wherein the guide element further comprises a guide element head having an insertion opening configured to receive a screw turning device.

7. The screw arrangement according to claim 6, wherein the guide screw further comprises a guide screw head that defines an opening in communication with the guide, and further comprising a cover removably coupled to the guide screw and configured to cover the opening.

8. The screw arrangement according to claim 7, wherein the guide screw further comprises cover screw threads that engage with the cover and are configured to run in a direction opposite the guide element threads and the inner guide screw threads, and wherein rotation of the cover causes the guide element threads to engage with the inner guide screw threads such that the screw arrangement can be unscrewed from the bone.

9. A screw arrangement for bone comprising:

an anchor screw having a first end that includes a guide element and an opposing, distal end that includes bone screw threads configured to anchor the anchor screw to bone; and a guide screw having bone screw threads configured to engage bone and a guide in which the anchor screw is received such that an overall length of the screw arrangement can be varied, the guide having a first portion in which the guide element feely slides and an additional portion in which the guide element is prevented from freely sliding, wherein the overall length of the screw arrangement is fixed when the guide element is in the additional portion, wherein the guide element further comprises a guide element head having an insertion opening configured to receive a screw turning device, wherein the guide screw further comprises a guide screw head that defines an opening in communication with the guide, and further comprising a cover removably coupled to the guide screw and configured to cover the opening, and wherein the guide screw further comprises cover screw threads that engage with the cover and are configured to run in a direction opposite the guide element threads and the inner guide screw threads, and wherein rotation of the cover causes the guide element threads to engage with the inner guide screw threads such that the screw arrangement can be unscrewed from the bone.

* * * * *